United States Patent [19]

Komatsu

[11] Patent Number: 4,802,847
[45] Date of Patent: Feb. 7, 1989

[54] DENTAL IMPLANT

[76] Inventor: Shigeru Komatsu, 7-14-7, Roppongi, Minato-ku, Tokyo, Japan

[21] Appl. No.: 97,618

[22] Filed: Sep. 16, 1987

[30] Foreign Application Priority Data

Nov. 28, 1986 [JP] Japan .................. 61-183392[U]

[51] Int. Cl.⁴ .................................................. A61C 8/00
[52] U.S. Cl. ................................................... 433/176
[58] Field of Search .......................................... 433/176

[56] References Cited

U.S. PATENT DOCUMENTS 3,729,825  5/1973  Linkow et al. ................ 433/176
3,798,771  3/1974  Edelman ......................... 433/176
3,977,081  8/1976  Zambelli et al. ................ 433/176
4,521,192  6/1985  Linkow .......................... 433/176

FOREIGN PATENT DOCUMENTS 3423752 10/1985  Fed. Rep. of Germany ...... 433/176

Primary Examiner—John J. Wilson
Attorney, Agent, or Firm—Scherlacher, Mok & Roth

[57] ABSTRACT

A dental implant includes a wavy or tortuous body. The body with a tortuous cross section has ridges extending from an upper end to a lower end. The dental implant also has a head supported on the upper end of the body and adapted to fit into an artificial tooth.

8 Claims, 2 Drawing Sheets

DENTAL IMPLANT

BACKGROUND OF THE INVENTION

1. Field of the Invention:

The present invention relates to an improvement in an dental implant for mounting an artificial tooth on an alveolar bone.

2. Description of the Relevant Art:

Dental implants comprise a body and a head supported on the body. In use, after the body of a dental implant has been embedded and fixed in a groove defined in an alveolar bone, an artificial tooth is fitted over the head.

Dental implants are available in various types and forms. One of such various implant types is known as a blade type implant. A wide variety of shapes of such blade type implants are described in "Comparative Clinical Implantology 1986-14", pages 14 through 18, and 67 through 83, published by Japan Medical Treatment Cultural Center on June 1, 1986, and "Dental Implants" written by Leonard I. Linkow and published in 1983. Blade type dental implants that have heretofore been proposed include bodies in the form of substantially flat plates with small surface irregularities.

To attach a blade type dental implant to an alveolar bone, a groove having a width and a length which correspond respectively to the thickness and the length of the body of the implant is defined in a portion of the alveolar body, where an artificial tooth is to be mounted, with a dental cutting tool, and then the body is inserted into the groove. Since the process of defining the bone in the alveolar body must be carried out in the patient's mouth, it is difficult to increase the dimensional accuracy of the groove. Inasmuch as the body of a conventional blade type dental implant is composed of a flat plate, the body cannot be firmly anchored in the groove unless the body is dimensionally accurately fitted in the groove. Therefore, a highly skilled technique is needed to firmly secure the dental implant to the alveolar bone without the danger of wobbling movement. For this reason, general dentists have not practiced much of dental implantation.

SUMMARY OF THE INVENTION

It is an object of the present invention to provide a dental implant which can relatively easily, safely, and firmly be anchored to an alveolar bone even by a general dentist, so that an artificial tooth can securely be mounted on the bone without wobbling movement and can be used for a long period of time.

According to the present invention, a dental implant comprises a body having a tortuous cross section with ridges extending from an upper end to a lower end, and a head supported on the upper end of the body and adapted to fit into an artificial tooth.

The above and further objects, details and advantages of the present invention will become apparent from the following detailed description of a preferred embodiment thereof, when read in conjunction with the accompanying drawings.

DETAILED DESCRIPTION OF THE PREFERRED EMBODIMENT

Figure 1:
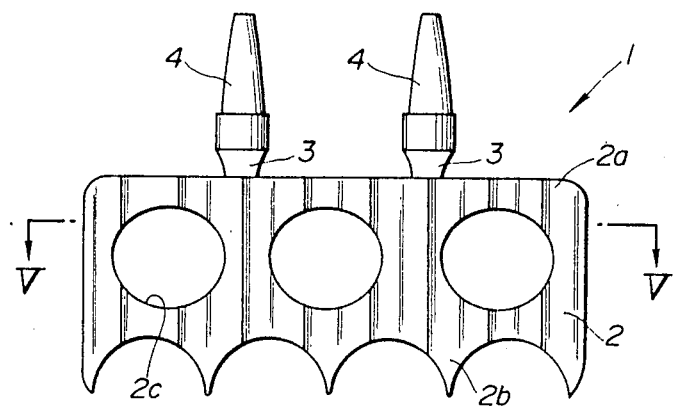
FIG. 1 is a front elevational view of a dental implant according to an embodiment of the present invention.
Figure 2:
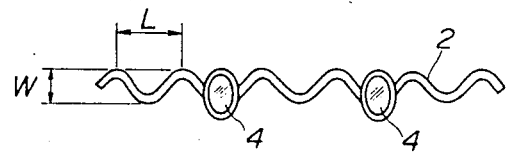
FIG. 2 is a plan view of the dental implant shown in FIG. 1.
Figure 3:
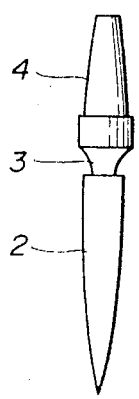
FIG. 3 is a side elevational view of the dental implant of FIG. 1.
Figure 4:
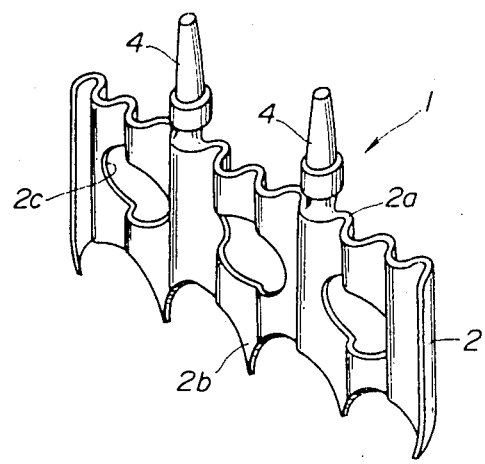
FIG. 4 is a perspective view of the dental implant of FIG. 1.
Figure 5:
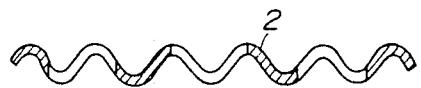
FIG. 5 is a cross-sectional view taken along line V—V of FIG. 1.

As shown in FIGS. 1 through 4, a dental implant 1 according to the present invention is made of a highly hard material such as a rare metal, e.g., titanium. The dental implant 1 includes a body 2 having a substantially uniform thickness and a continuous wavy or tortuous cross-sectional shape, as shown in FIG. 2. The wavy body 2 has a plurality of parallel ridges extending from a shoulder 2a at an upper end thereof toward a leg 2b at a lower end thereof, the tortuous cross section being continuous transversely to the ridges. Therefore, the body 2 has a plurality of vertically extending convexes and concaves on its face and back. The wavy configuration of the body 3 has a width W (FIG. 2) which should preferably range from 1 to 2 mm dependent on the number and type of artificial teeth to be fixed to the dental implant 1. Two adjacent crests of the wavy shape of the body 3 are spaced from each other by a distance L which should preferably range from 2 to 3 mm.

The body 2 has a plurality of openings or vents 2c. After the body 2 is embedded in an alveolar bone, opposite sides of the bone will meet and be joined to each other through the openings 2c on new bone growth so that the body 2 can firmly be anchored in place in the bone. The leg 2b is divided into a plurality of pointed leg portions for allowing the body 2 to be smoothly inserted into a groove defined in the alveolar bone when the body 2 is forced thereinto. As shown FIG. 3, the width of the wavy body 2 is progressively smaller from the upper end toward the lower end, with the result that the body 2 is of a wedge shape when viewed in side elevation.

The shoulder 2a of the body 2 supports thereon two spaced necks 3 on which heads 4 for mounting artificial teeth thereon are supported, respectively, thereon. As shown in FIG. 2, the head 4 has a generally elliptical cross section with its major axis extending substantially normal to a central plane of the body 2. While the two heads 4 are shown in the illustrated embodiment, the number of heads 4 used may be selected according to the number of artificial teeth to be mounted. The length of the body 2 is determined dependent on the number of heads 4 used.

Figure 6:
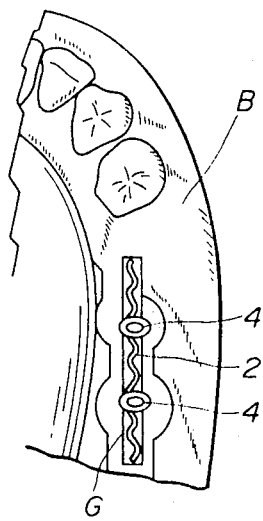
FIG. 6 is a fragmentary plan view showing the dental implant of FIGS. 1 through 4 which is embedded in a alveolar bone.
Figure 7:
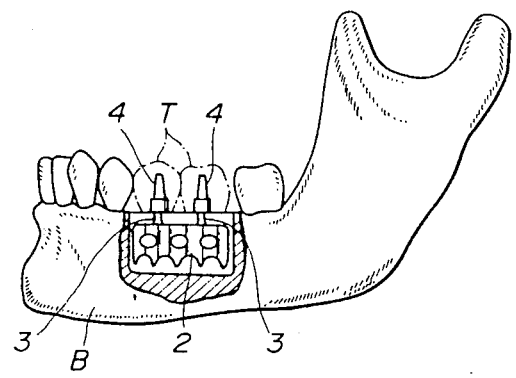
FIG. 7 is a front elevational view, partly in cut away, of the dental implant as embedded in the bone.

For anchoring the implant blade 1 to an alveolar bone, a groove G is defined in a portion of the alveolar bone B, where artificial teeth T are to be mounted, using a dental cutting tool, as shown in FIGS. 6 and 7, the groove G having a width slightly smaller than the width W of the body 3 and a length slightly larger than the length of the body 3, and the body 2 is forcibly inserted into the groove G. Even if the width of the groove G is somewhat larger than desired or the depth thereof greater than desired, such a dimensional error of the groove G can be absorbed by a slight deformation of the body 2 produced when forcing the body 2 into the groove G insofar as the groove width is smaller than the width W of the wavy body 2. Because of this together with the fact that the body 2 is made of a highly hard material such as titanium, the blade 1 is firmly fixed in the groove G at a prescribed depth.

The cross-sectional shape of the body 2 is illustrated as being continuously wavy or tortuous, and each of the crests of the wavy form is shown as being of a curved shape. However, the body 2 is not limited to such configurations, but may have a discrete wavy or tortuous shape, and may be of a triangular wavy shape.

With the arrangement of the present invention, as described above, the dental implant can relatively easily and firmly be secured in place even if the groove for receiving the body of the implant is subjected to a slight dimensional error. Therefore, dental implantation which has heretofore been difficult to perform can easily and safely be carried out by general dentists. By using dental implants of the present invention, patients are free from removable dentures which have conventionally been widely employed, and can eat foods with the firmly anchored artificial teeth in the same manner as with natural teeth.

Although there has been described what is at present considered to be the preferred embodiment of the present invention, it will be understood that the invention may be embodied in other specific forms without departing from the spirit or essential characteristics thereof. The present embodiment is therefore to be considered in all aspects as illustrative, and not restrictive. The scope of the invention is indicated by the appended claims rather than by the foregoing description.

I claim:

1. A dental implant comprising:
   a body having a tortuous cross section with ridges extending from an upper end to a lower end, and a plurality of pointed leg portions at the lower end; and
   a head supported on the upper end of the body and adapted to receive an artificial tooth, said head having a generally elliptical transverse cross section with its major axis extending substantially normal to a central plane of said body and a positioning step formed at the lower peripheral portion thereof for engaging the bottom portion of an artificial tooth.

2. A dental implant according to claim 1, wherein said tortuous cross section is continuous transversely to the ridges of said body.

3. A dental implant according to claim 1, wherein said tortuous cross section has a width in the range of from 1 to 2 mm.

4. A dental implant according to claim 1, wherein said tortuous cross section has a plurality of crests, adjacent ones of which are spaced a distance ranging from 2 to 3 mm.

5. A dental implant according to claim 1, wherein said tortuous cross section has a width which is progressively smaller from an upper portion to a lower portion of said body.

6. A dental implant according to claim 1, wherein said tortuous cross section has a plurality of crests each having a curved shape.

7. A dental implant according to claim 1, wherein the dental implant is made of a pure rare metal.

8. A dental implant according to claim 7, wherein said rare metal is pure titanium.

* * * * *